US006758817B1

(12) United States Patent
Pruter et al.

(10) Patent No.: US 6,758,817 B1
(45) Date of Patent: Jul. 6, 2004

(54) METHOD AND DISPOSABLE APPARATUS FOR GUIDING NEEDLES

(75) Inventors: Rick L. Pruter, Iowa City, IA (US); Quanah Lee Bain, Cedar Rapids, IA (US)

(73) Assignee: Protek Medical Products, Inc., Iowa City, IA (US)

( * ) Notice: Subject to any disclaimer, the term of this patent is extended or adjusted under 35 U.S.C. 154(b) by 35 days.

(21) Appl. No.: 10/065,029

(22) Filed: Sep. 11, 2002

(51) Int. Cl.[7] .................................................. A61B 8/14

(52) U.S. Cl. ...................................................... 600/461

(58) Field of Search ................................ 604/110, 197, 604/198; 600/461, 437, 462, 464, 565–567, 576–581

(56) References Cited

U.S. PATENT DOCUMENTS

| 2,451,183 A | 10/1948 | Tantimonaco |
| 2,536,963 A | 1/1951 | Stephens |
| 3,017,887 A | 1/1962 | Heyer |
| 3,538,915 A | 11/1970 | Frampton et al. |

(List continued on next page.)

FOREIGN PATENT DOCUMENTS

WO      WO 99/34735      7/1999

OTHER PUBLICATIONS

"Hitting the Mark with Realtime Guidance", Civco PROgram, Drawer Q, Kalona, IA 52247.
"ultrasoundsupplies.com" brochure of Civco Medical Instruments Co.
"General Purpose Needle Guides and Transducer Covers" brochure of Civco Medical Instruments, Sonosite Cross–Reference Information.

"Needle Guidance Systems, Transducer Covers, GE Medical Systems", gemedicalsystems.com brochure of Civco Medical Instruments, Solutions for Imaging.
UltraGuide 1000 System 4–page brochure, UltraGuide Ltd., Tirant Hacarmel Industrial Park, PO Box 2070, Tirat Hacarmel 30200, Israel.
UltraGuide 1000 2–page brochure, UltraGuide Ltd., Tirat Hacarmel Industrial Park, PO Box 2070, Tirat Hacarmel 30200, Israel.
Three–page web page of amedic.se printed on Nov. 5, 2002.
Disposable Transrectal Needle Guide, Civco Medical Instruments Co., Inc., Medical Parkway, 102 Highway 1 South, Kalona, IA 52247.
Maggi & Maggi II Plus, Sterile General Purpose Biopsy Needle Guides, Civco Medical Instrument Co., Inc., Medical Parkway, 102 Highway 1 South, Kalona, IA 52247.
Aloka Needle Guide/Probe Cover Kits, Civco Medical Instruments Co., Inc., Medical Parkway, 102 Highway 1 South, Kalona, IA 52247.
Multi Pro 2000, Multi–Purpose Ultrasound Linear Tracking Instrument, Civco Medical Instruments Co., Inc., 418 B Avenue, Kalona, IA 52247.
"US–Guide, Free–hand Guidance for Ultrasound Interventions" brochure from UltraGuide Smart Guidance Solutions.
"Dedicated Breast Ultrasound, USI Introduces A Revolution In Breast Ultrasound . . . Vista" by USI The Breast Imaging Co.

(List continued on next page.)

Primary Examiner—Dennis W. Ruhl
Assistant Examiner—Ruby Jain
(74) Attorney, Agent, or Firm—Simmons, Perrine, Albright & Ellwood, P.L.C.

(57) ABSTRACT

An apparatus and method for guiding a needle in conjunction with a biopsy using a medical imaging device, where a non-reusable needle guide, which is relatively inexpensive which grasps the sheathed bracket firm, and holds the same in a set position based upon a bullet-nose lock.

9 Claims, 6 Drawing Sheets

U.S. PATENT DOCUMENTS

| | | | |
|---|---|---|---|
| 3,556,079 A | | 1/1971 | Omizo |
| 4,029,084 A | | 6/1977 | Soldner |
| 4,058,114 A | | 11/1977 | Soldner |
| 4,108,165 A | | 8/1978 | Kopp et al. |
| 4,132,496 A | | 1/1979 | Casto |
| 4,249,539 A | | 2/1981 | Vilkomerson et al. |
| 4,289,139 A | | 9/1981 | Enjoji et al. |
| 4,332,248 A | | 6/1982 | DeVitis |
| 4,363,326 A | | 12/1982 | Kopel |
| 4,402,324 A | | 9/1983 | Lindgren et al. |
| 4,408,611 A | | 10/1983 | Enjoji |
| 4,469,106 A | | 9/1984 | Harui |
| 4,489,730 A | | 12/1984 | Jingu |
| 4,491,137 A | | 1/1985 | Jingu |
| 4,497,325 A | | 2/1985 | Wedel |
| 4,504,269 A | | 3/1985 | Durand |
| 4,542,747 A | | 9/1985 | Zurinski et al. |
| 4,567,896 A | * | 2/1986 | Barnea et al. ............... 600/443 |
| 4,635,644 A | | 1/1987 | Yagata |
| 4,742,829 A | | 5/1988 | Law et al. |
| 4,781,067 A | | 11/1988 | Cichanski |
| 4,838,506 A | * | 6/1989 | Cooper ........................ 248/200 |
| 4,865,590 A | * | 9/1989 | Marmar ....................... 604/180 |
| 4,877,033 A | * | 10/1989 | Seitz, Jr. ...................... 600/441 |
| 4,883,059 A | * | 11/1989 | Stedman et al. ............. 600/437 |
| 4,898,178 A | | 2/1990 | Wedel |
| 4,899,756 A | | 2/1990 | Sonek |
| 4,911,173 A | * | 3/1990 | Terwilliger ................. 600/464 |
| 4,970,907 A | | 11/1990 | Flynn |
| 5,052,396 A | * | 10/1991 | Wedel et al. ................ 600/461 |
| 5,076,279 A | | 12/1991 | Arenson et al. |
| 5,088,178 A | * | 2/1992 | Stolk ............................ 29/453 |
| 5,088,500 A | | 2/1992 | Wedel et al. |
| 5,161,764 A | | 11/1992 | Roney |
| 5,235,987 A | * | 8/1993 | Wolfe ......................... 600/461 |
| 5,343,865 A | | 9/1994 | Gardineer et al. |
| D362,064 S | | 9/1995 | Smick |
| 5,469,853 A | * | 11/1995 | Law et al. ................... 600/463 |
| 5,623,931 A | | 4/1997 | Wung et al. |
| D383,968 S | | 9/1997 | Bidwell et al. |
| 5,758,650 A | * | 6/1998 | Miller et al. ................ 600/461 |
| 5,871,448 A | | 2/1999 | Ellard |
| 5,910,113 A | * | 6/1999 | Pruter ........................ 600/437 |
| 5,924,992 A | * | 7/1999 | Park et al. ................... 600/461 |
| 5,941,889 A | | 8/1999 | Cermak |
| 5,968,016 A | * | 10/1999 | Yerfino et al. .............. 604/177 |
| D424,693 S | | 5/2000 | Pruter |
| 6,095,981 A | * | 8/2000 | McGahan .................... 600/461 |
| 6,102,867 A | * | 8/2000 | Dietz et al. ................. 600/461 |
| 6,139,544 A | | 10/2000 | Mikus et al. |
| 6,203,499 B1 | | 3/2001 | Imling et al. |
| 6,296,614 B1 | * | 10/2001 | Pruter ........................ 600/461 |
| 6,311,084 B1 | | 10/2001 | Cormack et al. |
| 6,361,499 B1 | * | 3/2002 | Bates et al. ................. 600/461 |
| 6,371,968 B1 | * | 4/2002 | Kogasaka et al. .......... 606/190 |
| 2001/0034530 A1 | | 10/2001 | Malackowski et al. |

OTHER PUBLICATIONS

Program for Medical Ultrasound Professionals, Winter 1995, Civco Medical Instrument Co., Inc., Medical Parkway, 102 Highway 1 South, Kalona, IA 52247.

"Ultra–Pro™ Sterile General Purpose Biopsy Needle Guide", CIVCO Medical Instruments Co., Medical Parkaw, 102 Highway 1 South, Kalona, IA 52247.

Solutions for Ultrasound, CIVCO Medical Instruments Co., Inc., Medical Parkway, 102 Highway 1 South, Kalona, IA 52247.

"Endocavity Needle Guide Kits" brochure of Civco Medical Instruments, copyright 2000, Solutions for Imaging.

"Civcoscan, Product News and Special Offers from CIVCO" brochure of Civco Medical Instruments, Winter 2001.

* cited by examiner

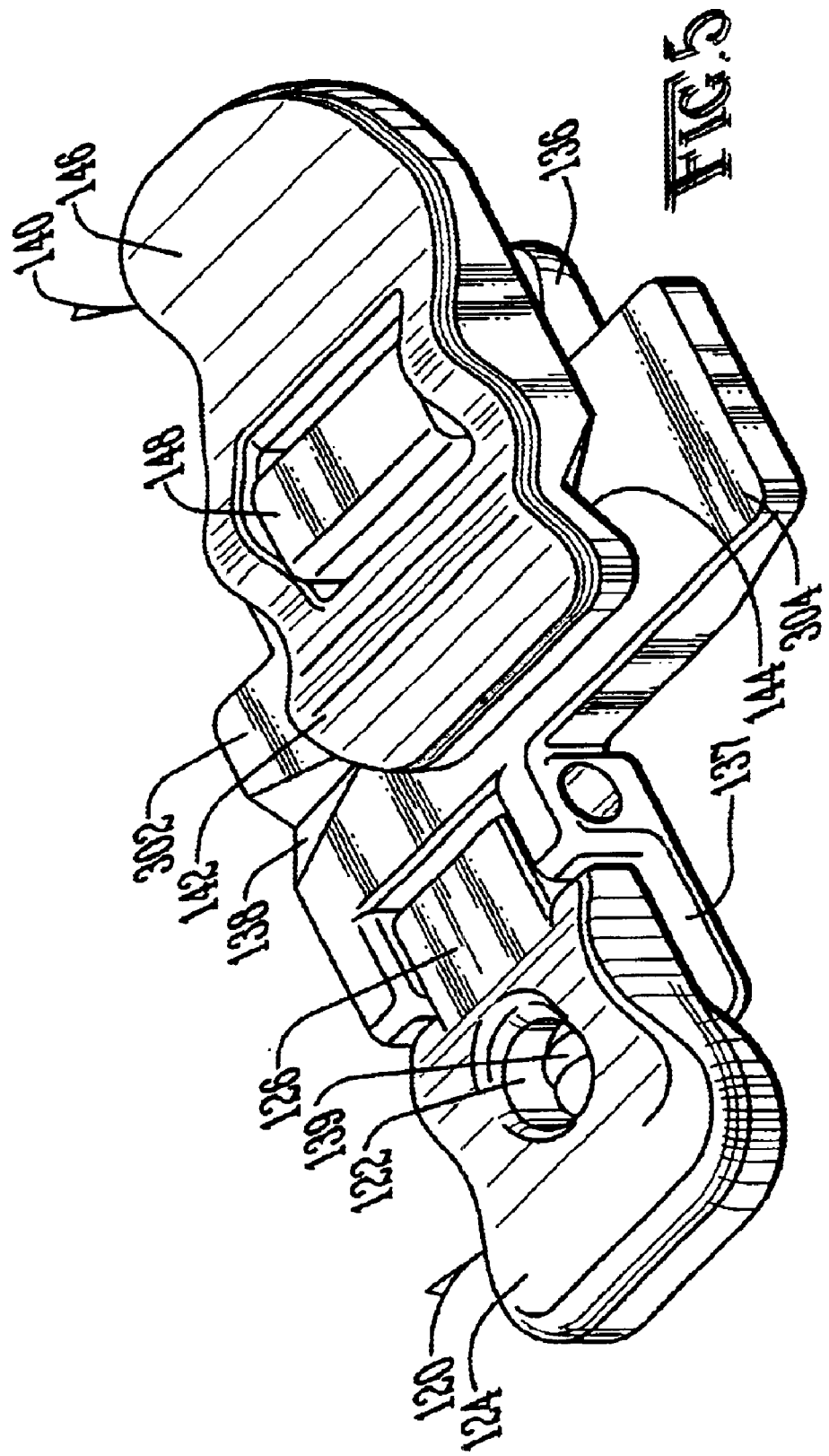

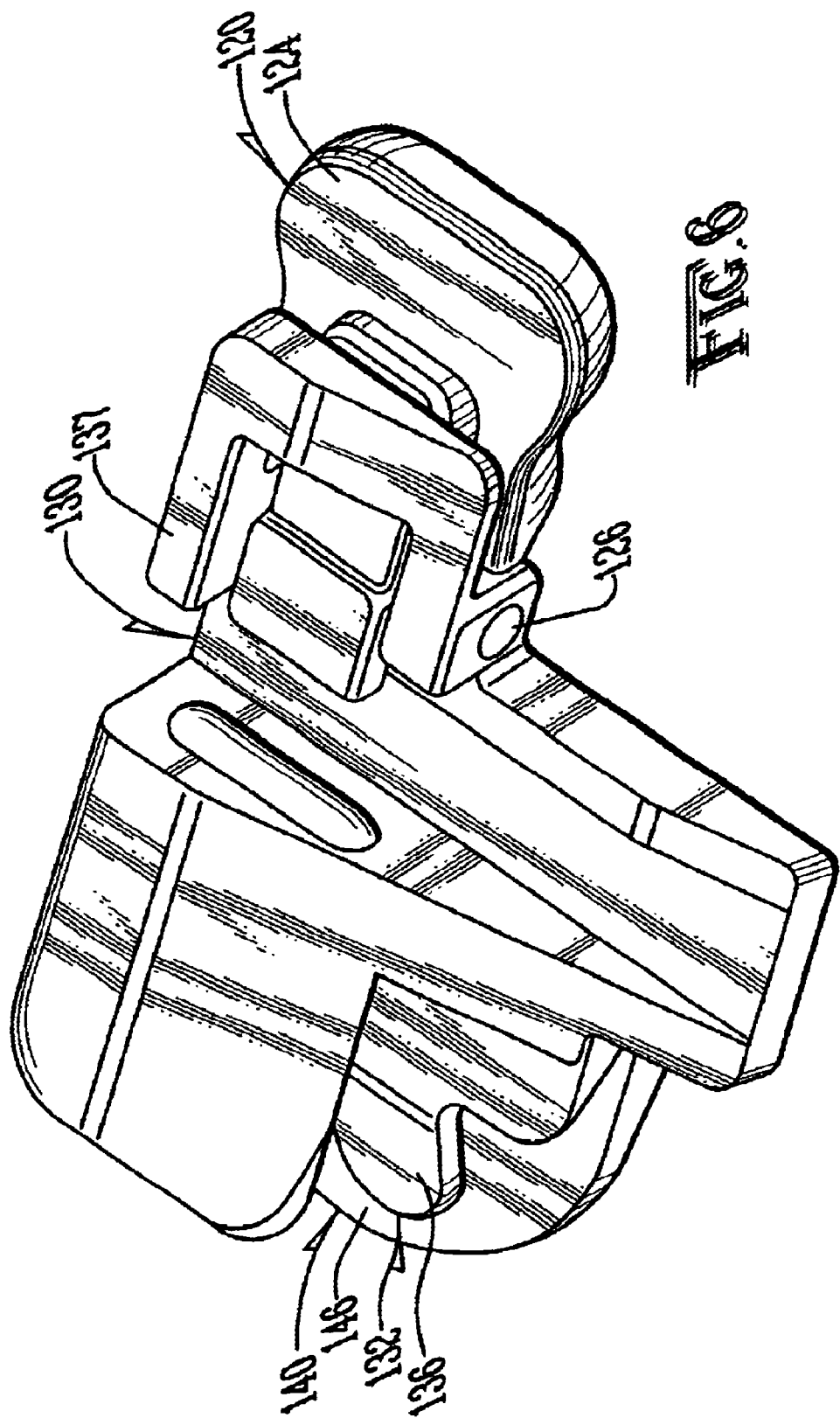

METHOD AND DISPOSABLE APPARATUS FOR GUIDING NEEDLES

BACKGROUND OF INVENTION

In recent years, handheld medical imaging transceivers, such as ultrasound and gamma ray transceivers, have been used extensively for various medical imaging situations.

In the past, the physician or medical professional typically will cover an ultrasound transceiver with a sterile sheath. Usually under the sheath is a mounting bracket attached to the transceiver. A needle guide is then typically attached over the sheath and coupled to the underlying bracket.

While these needle guides have been used extensively in the past, they do have some drawbacks. First of all, these needle guides require considerable attention and hand-to-eye coordination to be properly used. Additionally, these types of needle guides are often relatively expensive.

Consequently, there exists a need for improved methods and apparatus for guiding needles in an efficient manner.

SUMMARY OF INVENTION

It is an object of the present invention to provide an apparatus and method for guiding a needle in an efficient manner.

It is a feature of the present invention to include a plastic spring-like member.

It is another feature of the present invention to include, on the front side of the needle path, an enlarged base for guiding a needle into a grasping mechanism.

It is another feature of the present invention to include an enlarged base on a backside of the needle path for protecting the sheath from puncture by the moving needle.

It is another feature of the present invention to include a base-to-bracket attachment mechanism which is adapted for positive attachment to the bracket with a predetermined grasping force in a non-reusable manner.

It is an advantage of the present invention to achieve improved efficiency in guiding needles.

The present invention is an apparatus and method for guiding needles, designed to satisfy the aforementioned needs, provide the previously stated objects, include the above-listed features, and achieve the already articulated advantages. The present invention is carried out in a "physician burden-less" manner in a sense that the burden on a physician or other medical professional in guiding needles during the process of insertion into the needle guide, has been greatly reduced. Additionally, the system is carried out in an inexpensive manner in the sense that the use of plastic members for providing spring biasing for a needle grasping member is used to replace expensive metal springs. Finally, the present invention is carried out in a disposable manner in the sense that the base and the clamp used to couple to the sheathed bracket are designed to be used only once and then discarded.

Accordingly, the present invention is an apparatus and method including a needle guide with a plastic biasing member, enlarged base portions, and base-to-bracket locks which are non-reusable.

BRIEF DESCRIPTION OF DRAWINGS

The invention may be more fully understood by reading the following description of the preferred embodiments of the invention, in conjunction with the appended drawings wherein:

FIG. 5 is a perspective view of an alternate embodiment of the needle guide of the present invention, which is configured to mate with a bracket different from the bracket depicted in FIG. 1.

FIG. 6 is a perspective view of a reverse side of the needle guide of FIG. 5.

DETAILED DESCRIPTION

Figure 1:
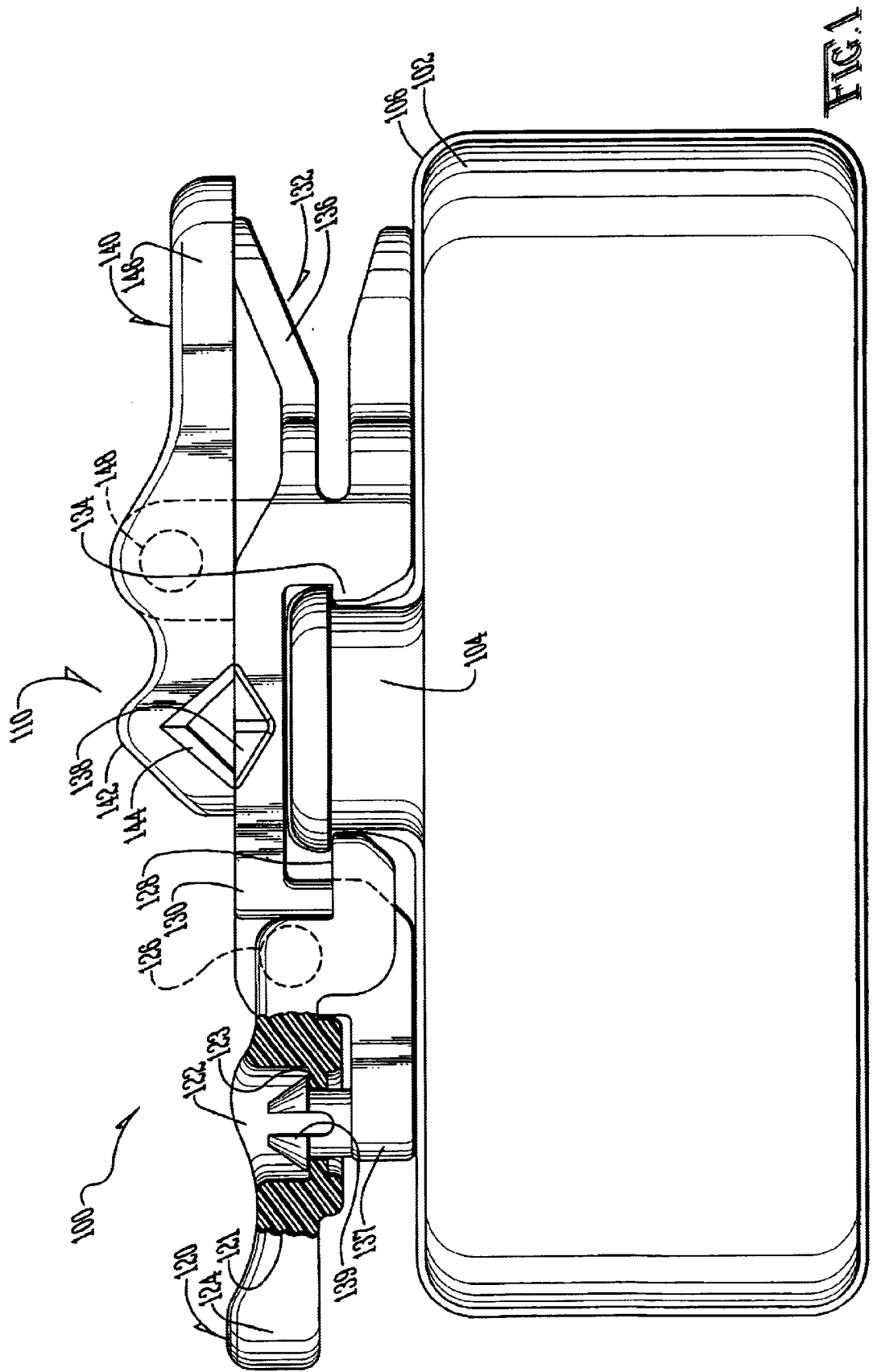
FIG. 1 is a partial cut-away side view of the apparatus of the present invention in a closed orientation.

Now referring to the drawings wherein like numerals refer to like matter throughout, and more specifically referring to FIG. 1, there is shown a needle guide, bracket and medical imaging transceiver system of the present invention generally designated 100. The system 100 includes a medical imaging transceiver 102 which could be any type of imaging system or device, and a transceiver bracket 104 which is coupled to said medical imaging transceiver 102 for the purpose of facilitating coupling with needle guides and other instruments. Transceiver bracket 104 can be coupled to medical imaging transceiver 102 in any suitable manner, such as clamps, screws, adhesive, etc. Transceiver/bracket covering sterile sheath 106 is disposed about transceiver bracket 104 and medical imaging transceiver 102 in a well-known manner. Needle guide assembly 110 is shown having a movable base portion 120, stationary base portion 130 and a needle grasping member 140, all of which could be made of any suitable material; however, a plastic material is preferred.

Movable base portion 120 includes a bullet-nose receiving hole 122 therein which, when viewed through the cut-away portion outlined by cut-away line 121, includes a bullet-nose removal inhibitor surface 123. Movable base portion 120 also includes a movable base handle end 124 which pivots about movable base pivot point 126. On an opposing end from movable base handle end 124 is movable base bracket grasping surface 128, which is configured to grasp a surface of transceiver bracket 104 when movable base handle end 124 is disposed in a closed and locked orientation.

Needle guide assembly 110 includes stationary base portion 130, which includes a stationary base biasing portion 132, which has a stationary base bracket mating portion 134 and a stationary base spring biasing member 136. Stationary base spring biasing member 136 is configured to provide a biasing force on needle grasping member 140. Stationary base portion 130 further includes a stationary lock end 137 having a bullet-nose lock male member 139. Bullet-nose lock male member 139 are well known in the art for providing positive attachment between items in a manner that separation of the items results in a destruction of the future capability of the bullet-nose lock male member 139 to firmly attach the items, which mates with bullet-nose removal inhibitor surface 123 of bullet-nose receiving hole 122 in movable base portion 120. Stationary base portion 130 further includes a stationary base needle entrance-guiding channel 138 disposed along an outside top edge of stationary base portion 130.

Disposed above stationary base portion 130 is needle grasping member 140, which has a needle grasping end 142 with a needle receiving void 144 therein disposed in axial alignment with stationary base needle entrance-guiding channel 138, so that a needle can be simultaneously in both stationary base needle entrance-guiding channel 138 and needle receiving void 144. Needle grasping member 140 includes a needle grasping member handle end 146, which when depressed toward stationary base biasing portion 132, causes needle grasping end 142 to pivot about needle grasping member pivot point 148. Stationary base spring biasing member 136 provides a resisting force upon needle grasping member handle end 146, which urges needle grasping end 142 into contact with stationary base portion 130.

Figure 2:
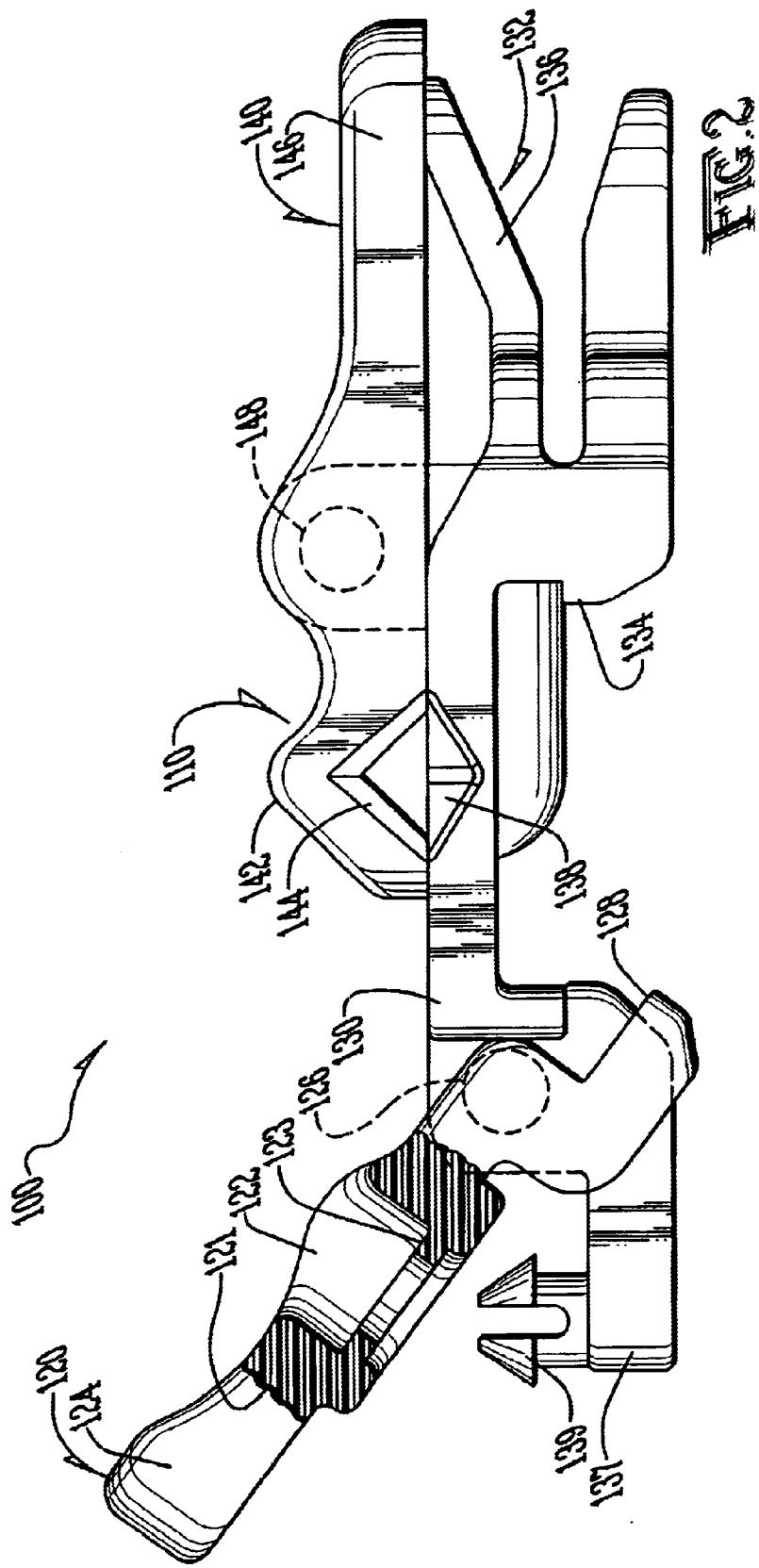
FIG. 2 is a side view of the needle guide of FIG. 1, in an open orientation prior to closing.

Now referring to FIG. 2, there is shown needle guide assembly 110 of FIG. 1 wherein movable base portion 120 is oriented in an open position prior to being closed and locked.

Figure 3:
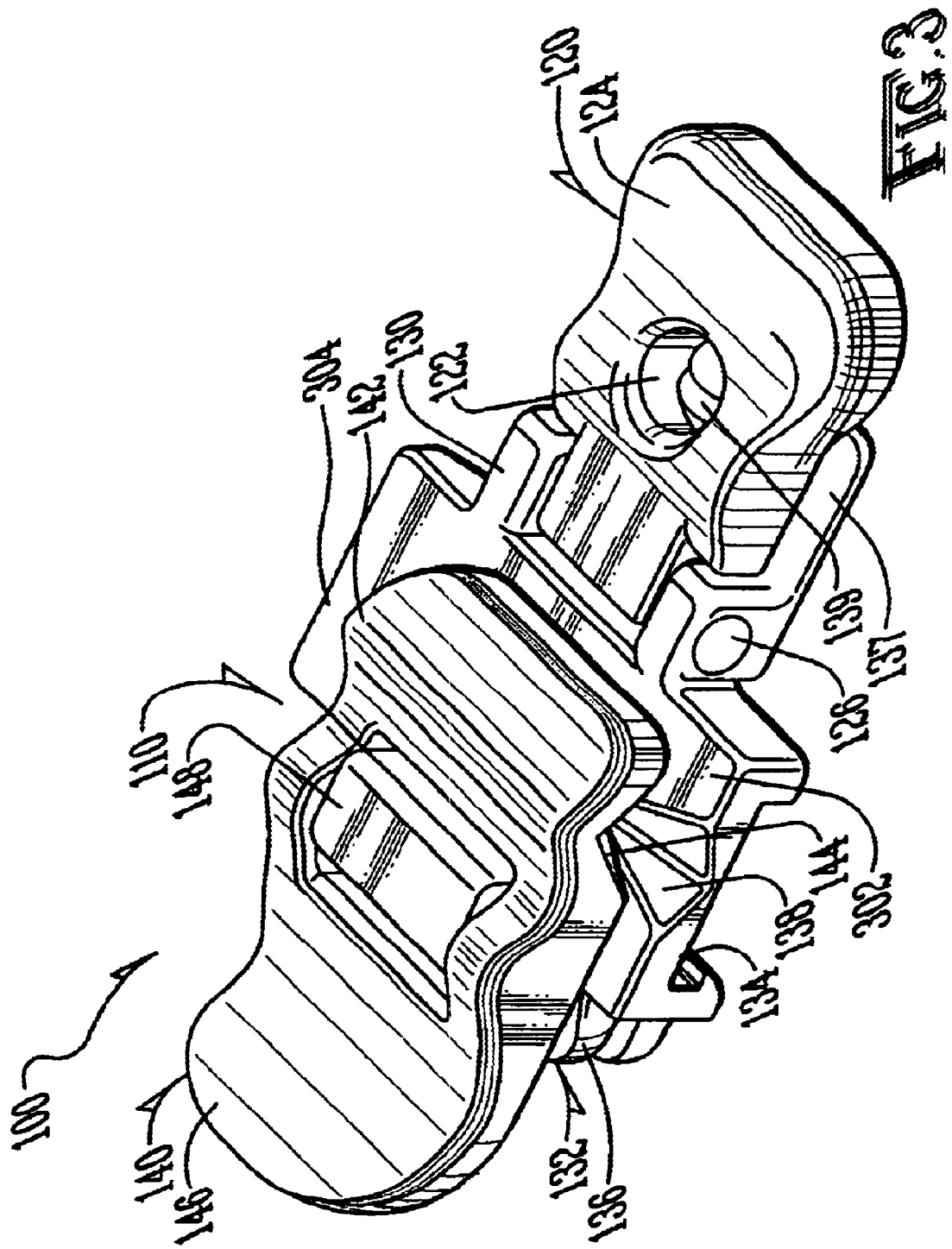
FIG. 3 is a perspective view of a needle guide of FIG. 2, which has a top enlarged sheath puncture protecting area and a bottom enlarged sheath puncture protecting area.

Now referring to FIG. 3, there is shown a perspective view of the needle guide assembly 110 of FIG. 2. Stationary base portion 130 is shown having a top enlarged sheath puncture protecting area 302 and a bottom enlarged sheath puncture protecting area 304. Top enlarged sheath puncture protecting area 302 and bottom enlarged sheath puncture protecting area 304 may be optional features, depending upon the particular needs of a particular application. Since the transceiver/bracket covering sterile sheath 106 (FIG. 1) is disposed adjacent to stationary base portion 130, the top enlarged sheath puncture protecting area 302 and the bottom enlarged sheath puncture protecting area 304 perform the functions of shielding transceiver/bracket covering sterile sheath 106 from puncture at a location of transceiver/bracket covering sterile sheath 106 where risk of puncture by the needle during insertion is highest. In a preferred embodiment, top enlarged sheath puncture protecting area 302 and bottom enlarged sheath puncture protecting area 304 extend at least one-fourth (¼) of an inch beyond the needle grasping member. In a most preferred embodiment of the present invention, top enlarged sheath puncture protecting area 302 extends at least three-eighths (⅜) of an inch beyond the needle grasping member 140.

Figure 4:
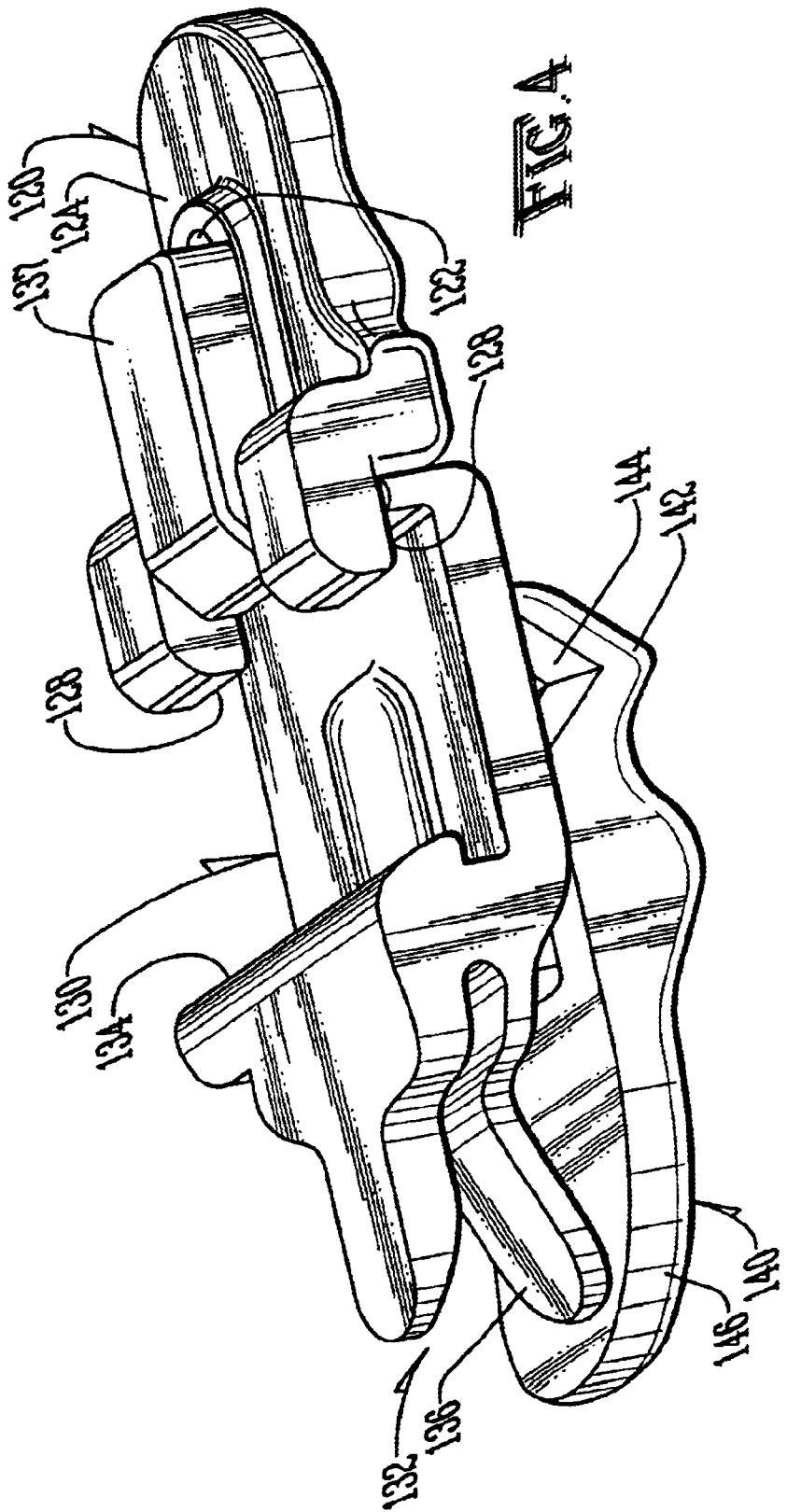
FIG. 4 is a perspective view of the reverse side of the needle guide of FIG. 1.

FIG. 4 is a perspective view of the reverse side of the needle guide of FIG. 1, in a closed and locked position.

FIG. 5 is a perspective view of an alternate embodiment of the present invention where the components labeled the same as in FIGS. 1–4 are similar in function, but have differing shape and orientation.

FIG. 6 is a reverse side of the needle guide of FIG. 5 which is obtained by rotating the device of FIG. 5 so that the opposite side of needle grasping member handle end 146 is found on the left side of the drawing.

In operation, the apparatus and method of the present invention as described and shown in FIGS. 1–3, could function as follows:

A transceiver bracket 104 is mounted on a medical imaging transceiver 102. A transceiver/bracket covering sterile sheath 106 is pulled over the medical imaging transceiver 102 and transceiver bracket 104 combination. Stationary base portion 130 is mated with transceiver bracket 104 by first engaging stationary base bracket mating portion 134 with transceiver bracket 104, and then movable base handle end 124 is pivoted so that movable base bracket grasping surface 128 contacts the sheathed transceiver bracket 104, and stationary lock end 137 is disposed adjacent the movable base handle end 124. Bullet-nose lock male member 139 is thereby inserted into bullet-nose receiving hole 122 and mates with bullet-nose removal inhibitor surface 123. A needle is placed against top enlarged sheath puncture protecting area 302 and moved into stationary base needle entrance-guiding channel 138 where it is readily guided into needle-receiving void 144. The needle exits needle-receiving void 144, traverses bottom enlarged sheath puncture protecting area 304, and is then available for interaction with a patient. Once the procedure is finished, the needle can be removed by pressing needle grasping member handle end 146, which causes needle grasping end 142 to move from stationary base portion 130, thereby permitting disengagement of the needle from the needle guide assembly 110.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. A medical imaging system comprising:
    a transceiver bracket coupled with a medical imaging transceiver;
    a transceiver/bracket covering sterile sheath disposed over said medical imaging transceiver and said transceiver bracket;
    a stationary base portion disposed over said transceiver/bracket covering sterile sheath and engaging said transceiver bracket via a first point of engagement and a second point of engagement;
    wherein said second point of engagement comprises a movable base portion which includes a movable base bracket grasping surface which mates with transceiver bracket and a movable base handle end, such that a manipulation of movable base handle end results in movement of movable base bracket grasping surface in and out of engagement with said transceiver bracket;
    a lock comprising a stationary component coupled to said stationary base portion and a movable component coupled to said movable base portion; one of said stationary component and said movable component having a resilient latch portion which mates with a latch mating surface, such that said resilient latch portion is mated with said latch mating surface until an unlatching force is applied to said resilient latch portion, such that permanent damage is done to said resilient latch portion, thereby permitting relative motion between said movable base portion and said stationary base portion and prohibiting future use of said stationary base portion and said movable base portion in a locked combination.

2. A system of claim 1 wherein said resilient latch portion is a bullet-nose male locking member.

3. A system of claim 1 further comprising a needle grasping member which is configured as a pivoting clamp to hold a needle in a defined location with respect to said stationary base portion.

4. A system of claim 3 wherein said stationary base portion comprises a top enlarged sheath puncture protecting area having a stationary base needle entrance-guiding structure coupled thereto, such that said stationary base needle entrance-guiding structure is oriented such that a needle placed therein receives guidance toward said defined location with respect to said stationary base portion.

5. A system of claim 4 further comprising a bottom enlarged sheath puncture protecting area disposed on said stationary base portion.

6. A system of claim 5 further comprising a plastic source of biasing force between said stationary base portion and said movable base portion.

7. A system of claim 6 wherein said resilient latch portion is a bullet-nose male locking member.

8. A medical imaging system comprising:

a medical imaging transceiver;

a transceiver bracket coupled to said medical imaging transceiver;

a transceiver/bracket covering sterile sheath disposed over said medical imaging transceiver and said transceiver bracket;

a stationary base portion, comprising a stationary base biasing portion which includes a stationary base spring biasing member;

said stationary base portion further comprising a stationary base bracket mating portion; a stationary lock end, having a bullet-nose lock male member thereon;

said stationary base portion further having a top enlarged sheath puncture protecting area having a stationary base needle entrance-guiding V-shaped channel therein;

said needle guide entrance-guiding V-shaped channel being V-shaped when viewed from at least two orthogonal directions;

a movable base portion, which is pivotally coupled to said stationary base portion at a movable base pivot point;

said movable base portion comprising a movable base handle end and a movable base bracket grasping surface which are on opposite sides of said movable base pivot point;

said movable base portion having a bullet-nose receiving hole therein which is configured to grasp said bullet-nose lock male member when inserted therein;

said bullet-nose lock male member being configured to grasp said bullet-nose receiving hole until a separation force is applied between said bullet-nose lock male member and said movable base handle end, which causes a permanent destruction of future locking capabilities of said bullet-nose lock male member;

a needle grasping member comprising a needle grasping end and a needle grasping member handle end, which are disposed on opposite sides of a needle grasping member pivot point;

said needle grasping end having a needle-receiving void therein which is disposed adjacent a vertex of said V-shaped channel in said top enlarged sheath puncture protecting area; and, said stationary base spring biasing member providing a biasing force causing a needle disposed in said V-shaped channel and said needle-receiving void to be retained by said needle grasping end.

9. A method of guiding a needle with respect to a medical imaging transceiver, comprising the steps of:

providing a medical imaging transceiver and a transceiver bracket disposed in a transceiver/bracket covering sterile sheath;

providing a stationary base portion having a stationary base bracket mating portion and a lock member;

engaging said stationary base bracket mating portion to said transceiver bracket;

moving a movable base portion, coupled to said stationary base portion such that a movable base bracket grasping surface on said movable base portion engages said transceiver bracket;

moving said movable base portion further such that said lock member prohibits said movable base portion from motion away from said stationary base portion, unless a force which permanently damages said lock member is applied thereto;

inserting a needle into a needle-retention area which is disposed outwardly of said stationary base portion;

performing a medical procedure using said needle and said medical imaging transceiver;

removing said needle from said needle-retention area;

applying a force on said lock member which permanently damages said lock member; and, discarding said lock member.

* * * * *